United States Patent
Ledergerber (10) Patent No.: US 6,921,418 B2
(45) Date of Patent: Jul. 26, 2005

(54) DUAL-SIDED, TEXTURIZED BIOCOMPATIBLE STRUCTURE

(75) Inventor: Walter J. Ledergerber, 31 Morningwood, Laguna Niguel, CA (US) 92677

(73) Assignee: Walter J. Ledergerber, Laguna Niguel, CA (US)

( * ) Notice: Subject to any disclaimer, the term of this patent is extended or adjusted under 35 U.S.C. 154(b) by 0 days.

(21) Appl. No.: 09/813,091

(22) Filed: Mar. 19, 2001

(65) Prior Publication Data

US 2001/0010024 A1 Jul. 26, 2001

Related U.S. Application Data

(63) Continuation of application No. 08/823,119, filed on Mar. 25, 1997, now Pat. No. 6,228,116, which is a continuation of application No. 08/472,781, filed on Jun. 7, 1995, now abandoned, which is a continuation-in-part of application No. 08/198,651, filed on Feb. 18, 1994, now Pat. No. 5,653,753, which is a continuation of application No. 07/837,284, filed on Feb. 18, 1992, now abandoned, which is a continuation of application No. 07/137,871, filed on Dec. 22, 1987, now Pat. No. 5,282,856.

(51) Int. Cl.[7] .............................. A61F 2/02; A61F 2/12; A61B 17/08
(52) U.S. Cl. .................. 623/11.11; 623/8; 606/151
(58) Field of Search .............................. 623/7, 8, 11.11, 623/7.8, 15.12; 606/151–157; 602/42, 52; 600/40; 428/36.5

(56) References Cited

U.S. PATENT DOCUMENTS

| | | | |
|---|---|---|---|
| 3,093,831 A | 6/1963 | Jordan | |
| 3,293,663 A | 12/1966 | Cromin | |
| 3,366,975 A | 2/1968 | Pangman | |
| 3,559,214 A | 2/1971 | Pangman | |

(Continued)

*Primary Examiner*—David J. Isabella
(74) *Attorney, Agent, or Firm*—O'Melveny & Myers LLP (57) ABSTRACT

A soft tissue expander has enhanced performance through use of differential and directional expandability, continuous expansion capability, increased base and dimensional stability, increased soft tissue purchase by virtue of unique surface topography, and results in improved cavity contour after expansion. Expansion means may be provided to expand the implant in a desired direction. In the preferred embodiment, an expander or implant has an exterior surface defining a volume, the exterior surface including a base portion, a first wall and a second wall, wherein the second wall is relatively thinner than the first wall. A fill port, which may be integrally molded into the expander, is included. As the expander is inflated, differential expansion occurs with the relatively thin second wall section expanding more than that of the first wall section. The base may include ribs or other molded-in structures to increase structural integrity. Optionally, a bellows may be included on the exterior surface of the expander, the bellows optionally including a limiting ring. Molded-in geometric patterns may be employed to present textured internal, as well as external surfaces to the implant or expander. Compressive structures may be used on the inside or outside surface of the implant.

12 Claims, 7 Drawing Sheets

U.S. PATENT DOCUMENTS

| | | | |
|---|---|---|---|
| 3,683,424 A | 8/1972 | Pangman | |
| 3,852,833 A | 12/1974 | Koneke et al. | |
| 4,019,209 A | 4/1977 | Spence | |
| 4,034,751 A | * 7/1977 | Hung | 602/52 |
| 4,175,557 A | * 11/1979 | Hung | 602/42 |
| 4,209,921 A | * 7/1980 | Kochauf | 38/97 |
| 4,264,990 A | 5/1981 | Hamas | |
| 4,289,125 A | * 9/1981 | Hung | 602/42 |
| 4,531,244 A | * 7/1985 | Hamas | 623/8 |
| 4,559,254 A | * 12/1985 | Suzuki | 428/131 |
| 4,573,999 A | * 3/1986 | Netto | 623/7 |
| 4,574,780 A | 3/1986 | Manders | |
| 4,605,412 A | 8/1986 | LaForest et al. | |
| 4,615,704 A | 10/1986 | Frisch | |
| 4,651,721 A | * 3/1987 | Mikulich et al. | 600/40 |
| 4,673,409 A | * 6/1987 | Van Kampen | 623/23.29 |
| 4,685,447 A | * 8/1987 | Iversen et al. | 623/8 |
| 4,743,480 A | * 5/1988 | Campbell et al. | 428/36.5 |
| 4,790,848 A | 12/1988 | Cronin | |
| 4,795,472 A | * 1/1989 | Crowninshield et al. | 623/23.29 |
| 4,816,339 A | 3/1989 | Tu et al. | |
| 4,865,603 A | * 9/1989 | Noiles | 623/23.5 |
| 4,899,764 A | 2/1990 | Gauger et al. | |
| 4,955,907 A | * 9/1990 | Ledergerber | 623/8 |
| 4,960,425 A | * 10/1990 | Yan et al. | 623/8 |
| 4,963,150 A | 10/1990 | Brauman | |
| 4,984,585 A | 1/1991 | Austad | |
| 5,022,942 A | 6/1991 | Yan et al. | |
| 5,026,394 A | 6/1991 | Baker | |
| 5,141,581 A | 8/1992 | Markham | |
| 5,207,709 A | * 5/1993 | Picha | 623/8 |
| 5,219,361 A | * 6/1993 | von Recum et al. | 623/8 |
| 5,447,535 A | 9/1995 | Muller | |
| 5,716,412 A | * 2/1998 | DeCarlo et al. | 623/23.5 |
| 5,892,621 A | * 4/1999 | McGregor et al. | 359/599 |

* cited by examiner

DUAL-SIDED, TEXTURIZED BIOCOMPATIBLE STRUCTURE

CROSS REFERENCE TO RELATED APPLICATIONS

This application is a continuation of U.S. application Ser. No. 08/823,119, filed on Mar. 25, 1997, now U.S. Pat. No. 6,228,116, which is a file wrapper continuation of U.S. application Ser. No. 08/472,781, filed on Jun. 7, 1995, now abandoned, which is a continuation-in-part of application U.S. Ser. No. 08/198,651, filed on Feb. 18, 1994, now U.S. Pat. No. 5,653,755, which is a continuation of U.S. application Ser. No. 07/837,284, filed on Feb. 18, 1992, now abandoned, which is a continuation of U.S. application Ser. No. 07/137,871, filed on Dec. 22, 1987, now U.S. Pat. No. 5,282,856, and is related to application Ser. No. 07/799,773, filed on Nov. 27, 1991, now U.S. Pat. No. 5,383,929, which is a continuation of U.S. application Ser. No. 07/325,444, filed on Mar. 20, 1989, now abandoned, which is a divisional of U.S. application Ser. No. 07/137,871, filed on Dec. 22, 1987, now U.S. Pat. No. 5,282,856, and further related to application Ser. No. 07/325,881, filed on Sep. 11, 1990, now U.S. Pat. No. 4,955,907, which is a divisional of U.S. application Ser. No. 07/137,871, filed on Dec. 22, 1987, now U.S. Pat. No. 5,282,856. The priority of these prior applications is expressly claimed and their disclosure are hereby incorporated by reference in their entirety.

FIELD OF THE INVENTION

This invention relates to implantable prosthetic devices. More particularly, it relates to implantable tissue expanders for use in plastic and reconstructive surgery to stretch tissue in order to augment a soft tissue deficit, cover an ablative defect, or reconstruct a portion of the body.

BACKGROUND OF THE INVENTION

Implantable prosthetic devices have been used in numerous locations in the body. The most common use has been for restoring or improving upon normal body contour or augmenting as well as reconstruction of the female breast. The most common breast prosthesis is similar to that disclosed in U.S. Pat. No. 3,293,663 to Cronin, in which there is a flexible elastomeric container, typically silicone, which is filled with a soft gel, typically silicone gel or a saline solution or a combination of both.

A tissue expander is surgically implanted beneath tissue to be stretched and is filled at appropriate intervals with biocompatible fluid. After sufficient stretch has been achieved the tissue expander is removed and the newly available tissue used to cover a soft tissue defect or used to create a replacement body part. A breast tissue expander may be made convertible to a definitive, long-term, augmentative prosthesis, also known as an "implant".

As the field has progressed from simple wound coverage to reconstructing more realistic body parts incorporating prosthetic devices, especially in the case of the female breast, it has become evident that more control of the expansion process would be desirable in order to speed the process, to minimize the morbidity and the number of surgeries involved, as well as to refine the end result.

In breast reconstruction, major problems associated with the tissue expansion process include difficulty in creating a normal teardrop shaped and normally pendant breast due to the inability to create a properly shaped pocket. Presently the only options are either multiply chambered expanders with multiple injection ports or laminated component structures. These are commercially considered less than desirable because they are prohibitively expensive. They are functionally suboptimal as slippage at the soft tissue/expander interface may occur and there is a lack of purchase at the interface which is associated with inappropriate thinning and grossly non-uniform expansion of tissue.

SUMMARY OF THE INVENTION

A soft tissue expander, which is a temporary implant into the body, utilizes structures having differential and directional expansion capability to project the expander or implant in the desired directions. In a preferred embodiment, an expander or implant has an exterior surface defining a volume, the exterior surface including a base portion, a first wall and a second wall, wherein the second wall is relatively thinner than the first wall. A fill port, which may be integrally molded into the expander, is included. As the expander is inflated, differential expansion occurs with the relatively thin second wall section expanding more than that of the first wall section.

The base may include ribs or other molded-in structures to increase structural integrity. Additionally, the base may include "toes" or other structures which project out from the base, such as flanges, which are adapted to provide a broader base or footprint to the expander. The expander enjoys increased base and dimensional stability as a consequence.

Additional directional expansion may be achieved through use of optional bellows molded into a portion of the expander shell wall. As the expander is inflated, the bellows provide a projection beyond that provided by the basic expander. Limiting rings may be used, such as surrounding the bellows at the bellow base which mates to the expander.

Molded-in geometric patterns may be employed to present varying textured surfaces to the internal or external surfaces of the implant or expander. This results in increased soft tissue purchase by virtue of unique surface topography and assists in obtaining differential expansion by virtue of the differential purchase resulting from the different molded-in patterns. Textured surfaces also have the effect of weakening periprosthetic scar tissue. Optionally, compressive structures may be beneficially used on the surface of the implant or in the interior of the implant.

In another preferred embodiment, a tissue expander uses multiple chambers wherein the chambers are in fluid communication. Preferably, one of the chambers is adapted for placement behind a muscle, such as the pectoralis muscle if the expander is used for breast reconstruction.

Accordingly, it is an object of this invention to provide an improved implant which functions as a soft tissue expander.

It is a further object of this invention to provide an enhanced ability to weaken periprosthetic scar as well as to permit the surgeon to improve cavity contour at the end of the expansion phase.

It is yet a further object of this invention to create variable yet controlled purchase at the tissue/expander interface and to provide for differential expansion capability by varying wall thickness. It is another object of this invention to provide for directional expandability of the expander.

It is an object of this invention to enable the surgeon to create a more natural soft tissue envelope for the human breast including a more natural inferior sulcus.

It is a further object of this invention to provide an implantable prosthesis which permits postimplantation accommodation of total volume, either more or less than the volume at implantation.

It is a further object of this invention to provide an implantable mammary prosthesis which permits post implantation accommodation of implant projection which is defined as the distance from the chest wall pole of the implant to the opposite pole of the implant.

DETAILED DESCRIPTION OF THE INVENTION

The present invention is based upon the previously disclosed method of liquid silicone molding of textured implants (my U.S. Pat. No. 5,354,338), directional expansion of implants and varying wall thickness (my U.S. Pat. No. 4, 955, 907), pressure adaptive structures, (my U.S. Pat. No. 5,383,929), as well as novel elements disclosed herein and methods of manufacture of the combination of elements.

The term implant is used broadly to include any foreign object which is inserted into the body. An expander is an object which is an implant because it is placed within the body. An expander is ordinarily placed within the body, and over time, such as a matter of weeks or a few months, is gradually inflated so as to expand and move adjacent soft tissues. After expansion, the expander may be removed from the body and the space filled with another implant, or optionally, the expander may be converted into a permanent implant in the body. In the latter case, this may involve changing the fluid in the implant/expander, such as from saline to a gel or a: triglyceride or other biocompatible fluid. Thus, the terms implant and expander are used interchangeably herein.

Figure 1:
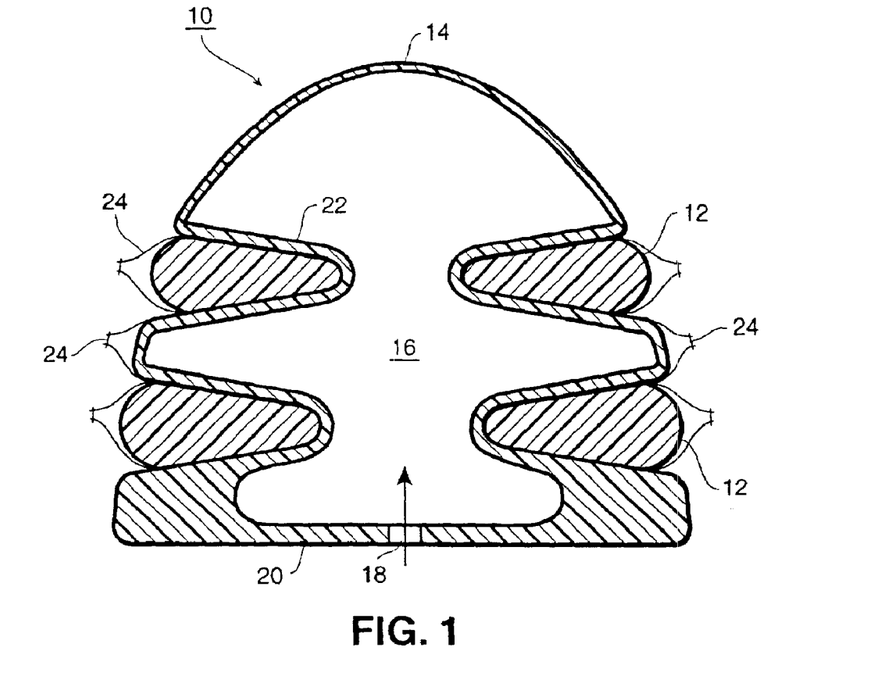
FIG. 1 is a cross-sectional view of a telescoping projection element of an implant or expander.

FIG. 1 shows a cross-section of a telescoping projection element which may be configured as the mammary prosthesis 10 proper or may be configured as a projection element of a more complex implant or expander. Toroid elements 12 may be solid or fluid-filled and serve to restrict horizontal displacement of the shell, yet permit vertical expansion.

The apical portion 14 of the expansion chamber 16 is made thin in order to permit preferential dilation of this region. The apical portion 14 is thin relative to other first wall portions 22. The fill port 18 serves to permit input of expansion fluid, which causes the expander to increase in volume, and to undergo differential expansion in the relatively thin wall, apical areas 14. A base region 20 is relatively thick and provides stability to the implant 10 when inserted in the body. Optionally, sheet teflon (PTFEe) 24 may be used to cover the toroidal regions 12.

Figure 2:
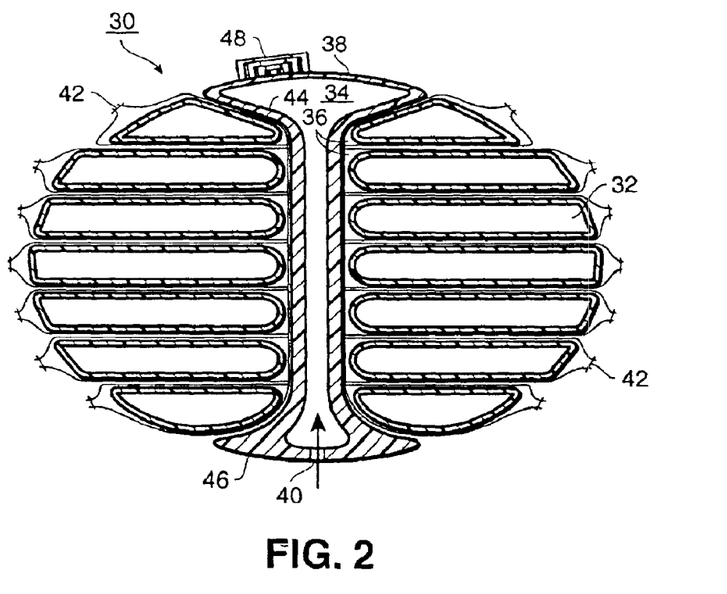
FIG. 2 is a cross-sectional view of an implant or expander including a telescoping projection element, where the apical portion of the expansion element is an expansion chamber.

FIG. 2 shows a cross-section of an implant 30 consisting of a stack of either hollow or solid toroid elements 32 held in apposition by a projection element 34 that traverses the central opening 36 of each toroid element 32 and which by virtue of the enlarged top and bottom portions serves to maintain all elements of the implant in intimate contact. The apical portion 38 of the projection element is an expansion chamber which may be filled through the bottom or top piece fluid port 40. The surfaces of the toroid elements are protected by a covering of PTFEe sheets 42 which are sewn or otherwise affixed to each other at the greater periphery. The tube is shown covered by tubular PTFEe to minimize friction. The apical portion 38 is relatively thin walled compared to first wall portions 44 or the based 46. Optionally, a biocompatible covering 48 may be added onto the implant 30.

Figure 3:
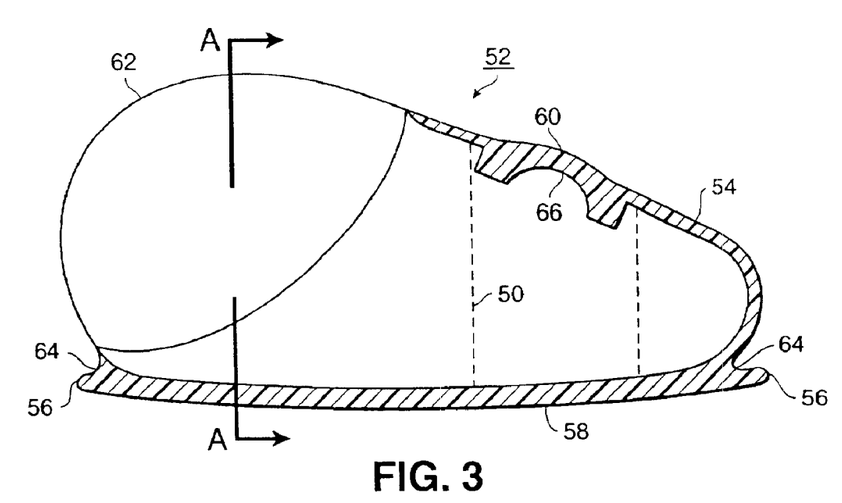
FIG. 3 is a cross-sectional view of an implant having variable wall thickness.
Figure 4:
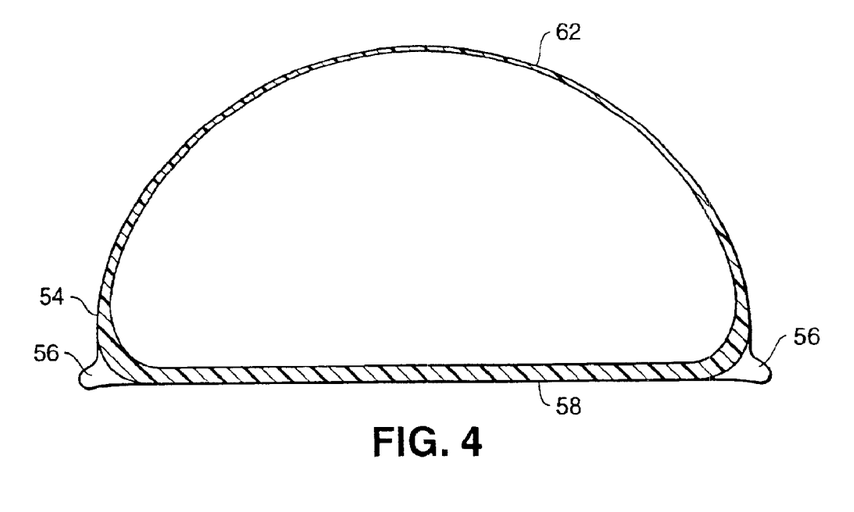
FIG. 4 is a cross-sectional view of FIG. 3 at line A—A.

FIGS. 3 and 4 show a cross-sectional and cut-away view at A—A of a preferred embodiment of a liquid silicon elastomer injection molded tissue expander. This structure is superimposed upon the "male" positive portion of the injection mold which produces the product. The "male" positive portion of the mold necessarily is supported by support column 50, shown in phantom.

The tissue expander 52 has continuously variable or varying wall thicknesses, however, in the preferred embodiment shown, there is a single, first thick region 54 of the implant incorporating substantially the smaller pole of the expander as well as extending to the "toe" 56 region of the base 58 and in the opposite direction from the smaller pole toward, and incorporating, the region of the fill port 60. The thin region 62 incorporates substantially the larger pole of the expander.

The "toe" region 56 is a molded flange-like extension of the integrally molded base 58 portion of the expander and is more generally described as an extension of any thickened portion of an expander. The functions of the "toe" region include: as an anchoring mechanism for the thick region of the expander as collagen matrix collects in space 64 which is defined as the recess between the "toe" (flange) 56 and the outer surface of the expander shell. Maturation of scar tissue results in increased tensile strength of the scar in space 64, which by shortening along the long circular axis of the scar, results in firm anchoring of the "toe," (flange) to the immediately adjacent tissues of the body.

The textured surface topography of the base region as well as all other texturized surface portions of the expander help to cause firm adherence between the expander and enveloping scar, as well as to disorganize scar, and thus weaken it. The "toe" (flange) 56 region assists greatly in maintaining dimensional as well as positional relationships. Upon surgical explanation of the tissue expander 52 the surgeon often reshapes the interior of the cavity created by the expander. The "toe" region, having formed a firm scar band in the region of the space 64, allows the surgeon the flexibility of conveniently creating more laxity of the wall of the cavity created by the expander by simply excising the scar band to the extent desired. By not excising the scar band thus formed the surgeon can limit the further stretching of the involved region of the cavity. It will be appreciated that the volume of scar and, therefore, the total tension in that scar is a direct function of the size/volume of space 64. The "toe" region 56 thus helps greatly in configuration angulation of the cavity margin.

Variably rounded peripheries of the base of a cavity can be engineered by varying base 58 thickness, expander wall 54 and 62 thickness, "toe," (flange) 56 thickness and length, differential expansion capability, degree of purchase at the tissue/expander interface, and volume/pressure relationships generated within the expander.

The injection fill port 60 of the expander is directly molded-in and thus incorporated into the molded shell structure of the tissue expander. In FIGS. 3 and 4, the fill port 60 is incorporated as a thickened cup-like region 66 of the molded integral tissue expander shell. This structure is fully disclosed in an application filed simultaneously with the present application, entitled "Injection Port for Implantable Tissue Expander." The position of the fill port 60 relative to any other structural element of the tissue expander is highly variable. In this embodiment, the void in the base created by the support column is patched with a separately molded silicone elastomer patch.

FIG. 4 shows the cross-sectional detail of FIG. 3 at line A—A. By way of example, for an expander useful for mammary reconstruction, the first wall 54 would be relatively thick, such as from 0.020 to 0.100 inches, and may have a thickness of approximately 0.030 inches. The second wall 62 would be relatively thinner, such as from 0.005 to 0.050 inches and would, for example, have a thickness of 0.020 inches. The base portion 58 may be of a different thickness, preferable relatively thick compared to the first wall 54 and second wall 62, and could be, for example, 0.050 inches thick.

Figure 5:
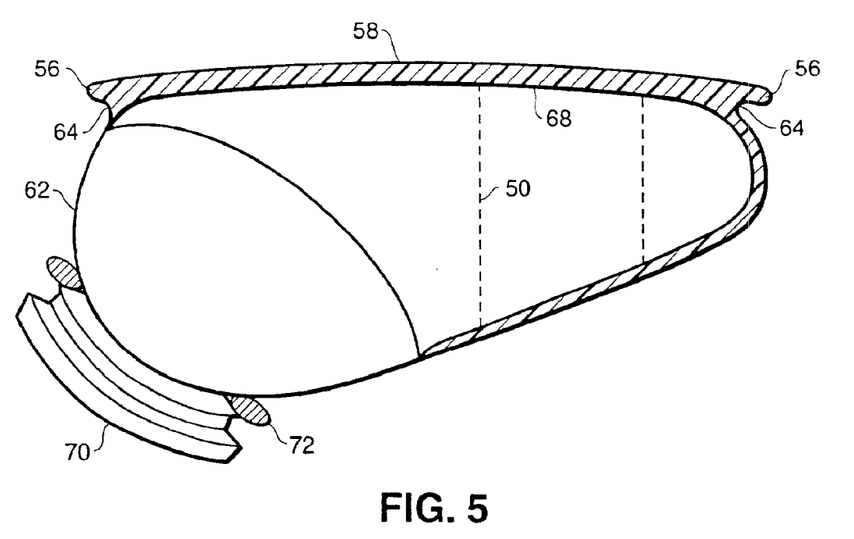
FIG. 5 is a cross-sectional view of an expander including a bellows expansion member.

FIG. 5 shows the "bellows" 70 structure as incorporated within the thin region 62 in this preferred embodiment but may be incorporated in any region of an expander where differential and directional expandability is required. Under internal pressure the limiting ring 72, which may be a separately molded silicone elastomer or another suitable material, restricts the expansion of the lesser diameter of the "bellows" 70 resulting in directional expansion of the bellows along an axis perpendicular to the plane of the limiting ring and away from the center of the expander lumen. The degree of directionality of expansion of the bellows is greater than is otherwise possible.

Figure 6:
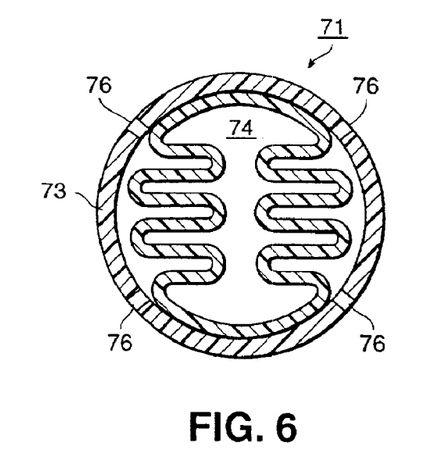
FIG. 6 is a cross-section of a pressure accommodation element.

FIG. 6 is a cross-sectional view of a compressive structure 70 which may optionally be inserted into a chamber, such as at 66 on FIG. 5. The pressure accommodation element may be affixed to the outer and/or inner surfaces of the shell or may be permitted to float freely within the saline or gel matrix within FIG. 6 is included to clarify the text pertaining to the comprehensive description of the invention. It must be clarified here that this structure is molded separately and adhesively secured to the internal surface of the expander not at the time of molding the expander shell, but rather at a later manufacturing step. A shell 72 preferably includes an evaginated insert 74 which contains gas or fluid. Optionally, openings 76 in the shell 72 permit flow to the insert 74.

The Pressure Adaptive Structure may be adhesively attached to the interior of the base of this embodiment. With reference to my U.S. Pat. No. 5,383,929, FIGS. 18, 22–24, the pressure adaptive structure illustrated in FIG. 6 is only one of many configurations of gas-filled structures well suited to serve the function of a "continuous" expanding structure within the tissue expander. For example, a curled sealed tubular gas-impervious structure, or a toroidal structure with the same characteristics would likewise suit the requirements for this structure: the ability to contain a biocompatible gas within the structure, which under the increased pressure exerted by the fluid during periodic augmentative filling causes the expander to partially collapse and in so doing compresses the gas substantially. The consequent increased pressure generated within the lumen of the pressure adaptive structure continues to exert outward pressure on the fluid in the lumen of the expander proper. At all times, the pressure inside the pressure adaptive structure and the pressure inside the lumen of the tissue expander proper are in equilibrium, however the gas-filled pressure adaptive structure exercises the necessary recoil needed to continue the expansion of the entire tissue expander in order to overcome the resistance offered by the tissues undergoing expansion.

Figure 7:
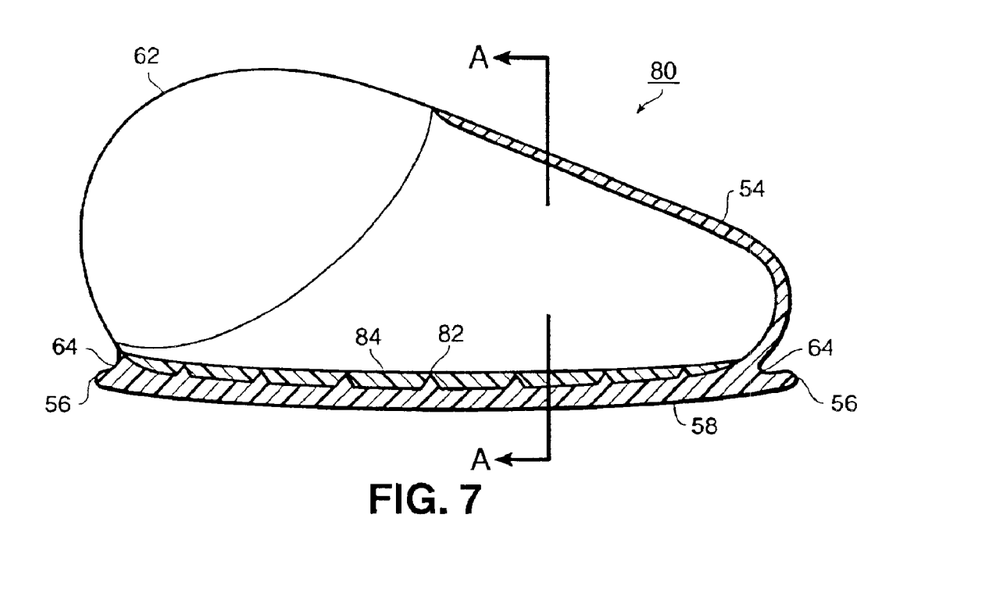
FIG. 7 is a cross-section of an expander having a base including integral ribs.
Figure 8:
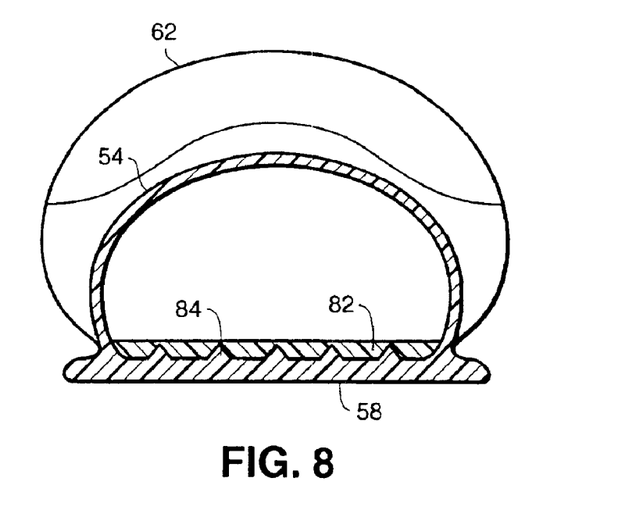
FIG. 8 is a cross-section of FIG. 7 at A—A.

FIG. 7 is a cross-section of an expander 80 having a base including integral ribs. FIG. 8 is a cross-section of FIG. 7 at A—A. In this structure, reinforcing ribs 82, 84 are integrally formed in the base 58 of the implant/expander 80. This provides relative rigidity to the structure. Optionally, the ribs may be formed in any direction, or in any pattern or configuration to achieve the desired rigidity. A shown, longitudinal ribs 82 run into the plane of FIG. 7 and traverse ribs 84 run parallel to the plane of FIG. 7.

Figure 9:
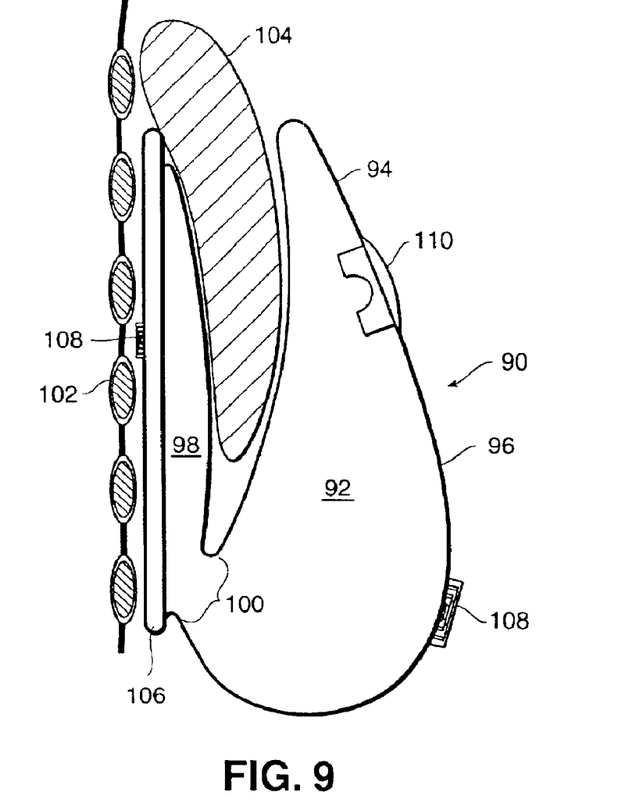
FIG. 9 is a cross-sectional view of a multi-chambered expander.

FIG. 9 is a cross-sectional view of a multi-chambered expander 90. While two chambers are shown in FIG. 9, more chambers 92 may be used consistent with the inventive concept. The first chamber comprises a relatively large chamber, and may incorporate a first relatively thick-walled portion 94, and a second relatively thin walled portion 96. The second chamber, or pumping chamber 98, is in fluid communication with the first chamber 92, such as at tube or passageway 100. For the application shown in FIG. 9, that is, expansion for breast reconstruction, the second chamber 98 is adapted for disposition between the ribs 102 and the pectoralis muscle 104. A base portion 106 is integral to the second chamber 98. Optionally, texturization 108 (shown partially covering the implant) may be formed over the surface of the implant, such as over the exterior disposed face of the implant, and on the exterior portion of the base 108 directed towards the chest wall. A fill port 110 is provided. It will be appreciated that the pumping function of the second chamber 98 in combination with pectoralis muscle 104 could also be preformed by a mechanical pump integrated into the system.

Figure 10:
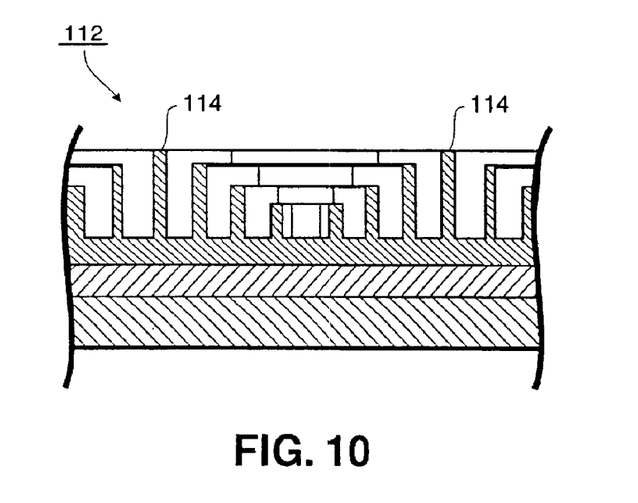
FIG. 10 is a cross-sectional view of a textured covering for use on the implant or expander.

FIG. 10 is a cross-sectional view of a textured covering for use on the implant or expander. The "nested hexcels" structural pattern 112 may be attached to or part of the implant. The textured covering may form the entirety or only a portion of the covering of the implant. The hexcel with the largest perimeter 114 in this configuration is also the tallest and delimits hexagonal pools of biologic materials and tissues at the interface between the implant and the body cavity. As scar tissue forms it is forced into concentric, nested rings of scar tissue which do not communicate freely and thus do not contribute to an integral circumferential scar capsule.

The height of these nested hexcels structures may be varied. Also, the number, diameter or perimeter of the hexcel structures as well as their wall thickness and shapes and characteristics may be varied. It will be further appreciated that a great number of geometric patterns may be utilized for the purposes described here, including square and circular patterns.

Various types of texturization are available. Using the preferred manufacturing technique of this invention, namely injection molding, the surface may easily be texturized with any desired form or pattern, whether predictable or random.

Method of Manufacture

The tissue expander is made of liquid silicone elastomer supplied by NuSil Technology of Carpinteria, Calif., and is described in product literature as Liquid Silicone Rubber MED-4840. The product is described as a two-part system which is Platinum cured. The pre-mixed liquid parts A and B are injected into a preheated mold which is then heated further to 275–320 degrees Fahrenheit. Curing time ranges between 5–10 minutes.

The molded product is removed from the mold and further vulcanized for 20–45 minutes in a separate oven at 275–375 degrees Fahrenheit. Molded voids in the shell are then patched with a silicone elastomer molded component. The tissue expander thus molded results in a variably textured and contoured shape with continuously variable wall thickness.

Optionally, the tissue expander may be molded with an integral chamber-like fill port incorporated directly into the whole structure at the time of molding. A fill port may be molded separately and during a later stage of manufacture be made adherent to the shell-like expander structure either totally on the smooth internal surface of the shell-like structure or with a portion of the fill port projecting through the shell-like structure.

Illustrated in FIGS. 3 and 5 are two preferred embodiments of a molding tool positive with a product of the molding process superimposed on the tool. FIG. 3 illustrates the case where a single void in the shell-like structure results from the molding process as a result of the presence of supporting column 50. This void is sized so as to accept a separately molded fill port, which is adhesively attached to the shell-like expander. FIG. 5 illustrates the case where a fully integrated fill port or other appended structure is molded directly into the expander proper.

In FIG. 3, a single resultant void is created at the region where supporting column 50 is attached to the positive portion of the molding structure. In FIG. 5, this void requires patching with a special silicone elastomer patch created specifically for this purpose. In addition to the positive portion of preferred-embodiment molds illustrated in FIG. 3, there are two "female" portions of the mold which serve to texturize the outer surface of the molded product. These female mold elements slide up and down guide shafts to fully enclose the positive mold element, or may slide in a plane substantially perpendicular to the axis of column. The variably dimensioned void between the positive (male) and "female" portions of the mold serve to define the variable wall thickness of the final molded silicone elastomer product. Unique texturing of the mold as per U.S. Pat. No. 5,354,338 is transferred to molded product in accordance with engineering specifications. Thin 62 and thick 54 regions of the wall of the balloon-like expander shell enable differential expansion, the thin region enhancing expansion, the thick regions inhibiting it. An additional preferred embodiment feature permitting especially advantageous directional expansion of a portion of a molded product is the bellows-like structure 70 molded directly into the "larger pole" apex of the tissue expander. A further preferred embodiment of a tissue expander is the inclusion of a gas-filled pressure adaptive structure (FIG. 6) within the lumen of the tissue expander as per my U.S. Pat. No. 5,383,929. This structure is indicated in FIG. 6, "pressure adaptive" structure and is adhesively attached to the interior surface of thick region.

The ability to extend the time intervals between periodic injections of filler fluid, by virtue of continuous outward pressure exerted by an integral gas-filled pressure chamber, makes the process more comfortable for the patient. Continuous expansion results in reaching final volume more quickly and is a clear advantage over existing technology.

Figure 11:
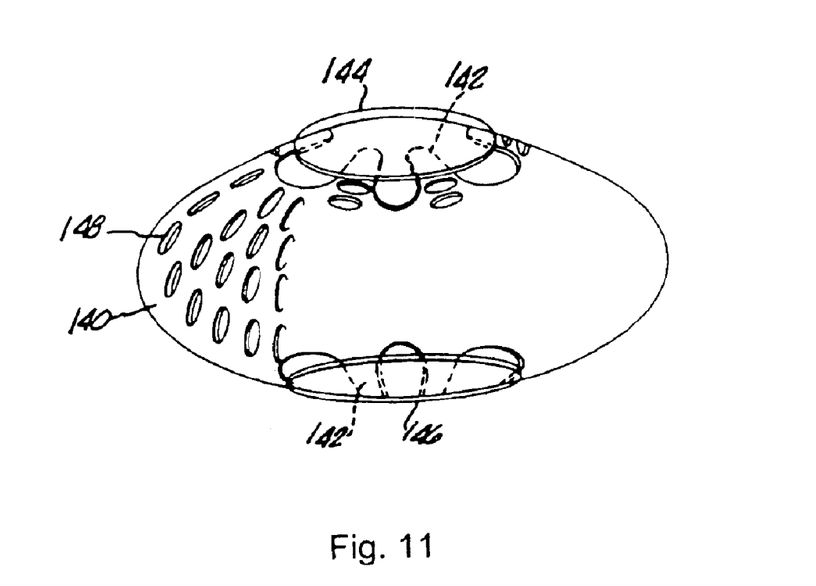
FIG. 11 is a perspective view of an implant covering cut from a single sheet of ePTFE placed around a silicone elastomer shell.
Figure 12:
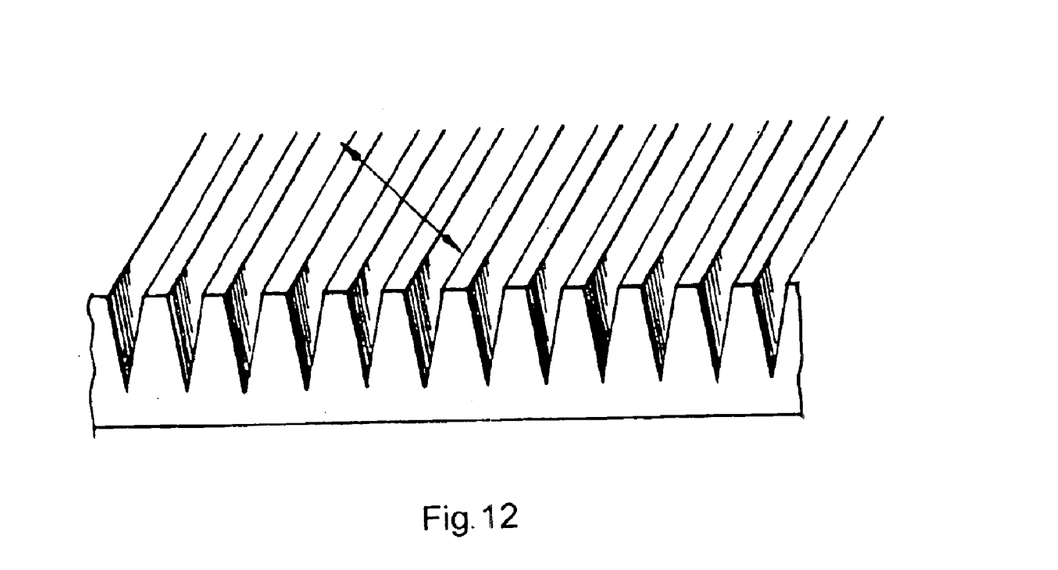
FIG. 12 shows a perspective view of detail of ePTEE sheet material with a partial thickness pattern of simple cuts and/or channels which results in numerous individual villi of ePTFE and great irregularity of the surface of the material. Additional patterns of cuts or troughs may be made along any other axis as indicated, for example, by the arrows.

A covering for an implant may be constructed substantially of a single sheet of ePTFE as shown for example in FIG. 4 11. A single sheet of ePTFE 140 Is cut so as to permit it to be wrapped around the implant 110. Projectile tongues 142 maybe fastened together or may be attached to separate ePTFE sheets 144 and 146 which serve as cap and bottom pieces. Appropriate cuts 148 are made in the single ePTFE sheet 140 to permit stretching of the sheet in various directions.

The implant coverings usable in connection with this invention may be manufactured from any material which promotes limited tissue ingrowth into the material, and has a high biocompatibility and low reactivity and disorganizes scar tissue at the implant/body interface. Expanded PTFE (ePTFE) is a preferred material for this invention. ePTFE is sold under the tradename Goretex and is readily available. The expanded ultrastructure of this material is associated with a high degree of ultramicroporosity which invites tissue ingrowth. The material is approximately 50% air by volume. It is extremely strong vet soft, smooth, pliable, compressible and stretchable. Goretex is readily available in sheet form of various thicknesses, as round filaments of various diameters, and as tubes of various diameters and wall thicknesses. ePTFE sheeting stretches to a limited extent alone a given axis, however resists stretching along all axes simultaneously. It is extremely biocompatible having been used in more than 700,000 clinical uses with no confirmed cases of material rejection. ePTFE is incorporated into surrounding tissue and is minimally encapsulated by collagen. The material is extremely strong and thereby would reduce the need for regeneration for material fatigue. It resists flexural fatigue by acting like a chain when bending forces are applied. However, it is easily cut by a knife or by using die cutting techniques. It lends itself well to machine manufacturing methods including stitching.

Figure 13:
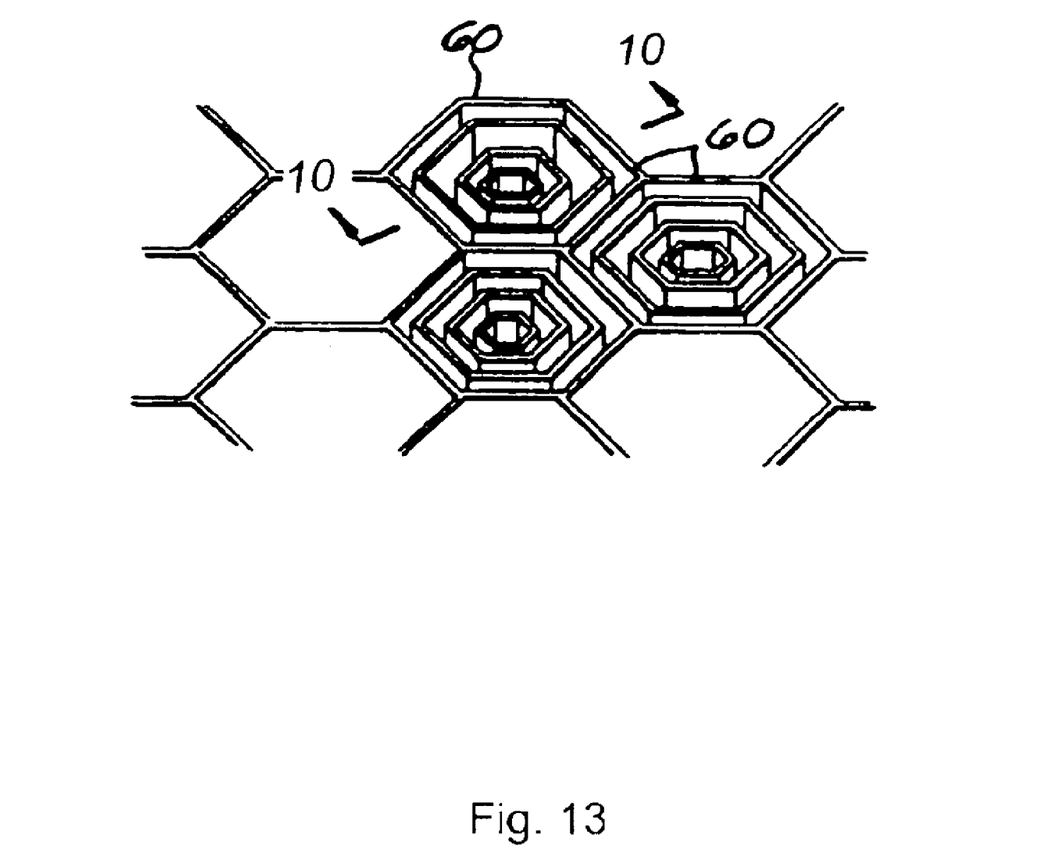
FIG. 13 shows a cover consisting of a molded silicone elastomer shell element with a pattern of nested hexagonal cells over the entire surface of the implant. Detail is shown. Other suitable geometric patterns may also be utilized.

As in FIGS. 10 and 13, a textured molded covering 112 may be provided made of silicone elastomer or other suitable materials which serves to limit the force of scar contracture around the implant by disorganizing the scar tissue itself and also by compartmentalizing blood clot and collagen around the implant.

The "nested hexcel" structural pattern of FIGS. 10 and 13 is a preferred embodiment. All such hexcels are attached to or part of the same base which is a covering element of the implant. The textured covering 112 may form the entirety or only a portion of the covering of the implant. The hexcel with the largest perimeter 60 in this configuration is also the tallest and delimits hexagonal pools of biologic materials and tissues at the interface between the implant and the body cavity. As scar tissue forms it is forced into concentric nested rings of scar tissue which do not communicate freely and thus do not contribute to an integral circumferential scar capsule.

It will be appreciated that the height of these nested hexcel structures may be varied. Also the number, diameter or perimeter of the hexcel structures as well as their wall thickness and shapes and characteristics may be varied. It will be further appreciated that a great number of geometric patterns may be utilized for the purposes described above, including square and circular patterns.

It will be appreciated also that the molded textured covering 112 above may be configured to accept a geometric shaped portion of any of the other coverings described herein. A piece of the woven ePTFE stretch weave cover, as an example, is sewn or otherwise suitably affixed to the molded covering 112.

Though the invention has been described with respect to specific preferred embodiments, many variations and modifications will become apparent to those skilled in the art. It is therefore the intention and expectation that the appended claims be interpreted as broadly as possible in view of the prior art in order to include all such variations and modifications.

What is claimed is:

1. An implantable sheet for implantation in a body comprising:
    an implantable sheet of ePTFE having a first surface and a second surface,
    the first surface being non-textured, and
    the second surface being textured, the second surface having:
        a plurality of continuous, parallel channels extending into the thickness dimension of the sheet, the channels being formed by cutting the second surface of the sheet,
        a plurality of ridges disposed between the channels, forming troughs and
        the second surface comprising a pattern of ridges and troughs, the pattern including a plurality of parallel wells.

2. The sheet of claim 1 wherein each channel has a cross-sectional dimension of varying width.

3. The sheet of claim 1 wherein the pattern is periodic.

4. The sheet of claim 1 wherein the pattern is repetitive.

5. The sheet of claim 1 wherein the pattern is uniform.

6. The sheet of claim 1 comprising a laminated structure.

7. The sheet of claim 1 wherein the plane of the ridge regions is substantially parallel to the plane of the trough regions.

8. The sheet of claim 1 wherein the second surface is arranged to stimulate high tissue ingrowth.

9. The sheet of claim 1 wherein the second surface is arranged to disorganize scar tissue.

10. The sheet of claim 1 wherein the channels and ridges are straight.

11. The sheet of claim 1 wherein the first surface is substantially planar.

12. The sheet of claim 1 wherein the channels comprise v-shaped cuts.

* * * * *